US010037825B2

(12) United States Patent
Hill

(10) Patent No.: US 10,037,825 B2
(45) Date of Patent: Jul. 31, 2018

(54) EMISSION MONITORING SYSTEM FOR A VENTING SYSTEM OF A NUCLEAR POWER PLANT

(71) Applicant: AREVA GMBH, Erlangen (DE)

(72) Inventor: Axel Hill, Stockstadt (DE)

(73) Assignee: AREVA GmbH, Erlangen (DE)

( * ) Notice: Subject to any disclaimer, the term of this patent is extended or adjusted under 35 U.S.C. 154(b) by 559 days.

(21) Appl. No.: 14/922,330

(22) Filed: Oct. 26, 2015

(65) Prior Publication Data

US 2016/0118149 A1    Apr. 28, 2016

Related U.S. Application Data

(63) Continuation of application No. PCT/EP2014/055804, filed on Mar. 24, 2014.

(30) Foreign Application Priority Data

Apr. 25, 2013    (DE) .................. 10 2013 207 595

(51) Int. Cl.
*G21C 17/00*    (2006.01)
*G21C 9/004*    (2006.01)
(Continued)

(52) U.S. Cl.
CPC ......... *G21C 17/002* (2013.01); *G01N 1/2247* (2013.01); *G21C 9/004* (2013.01);
(Continued)

(58) Field of Classification Search
CPC .. G01N 1/2247; G21C 13/022; G21C 17/002; G21C 17/028; G21C 9/004
(Continued)

(56) References Cited

U.S. PATENT DOCUMENTS 4,493,792 A * 1/1985 Graf ................. G21F 7/068
                                                    376/203
5,267,282 A   11/1993 Labno et al.
(Continued)

FOREIGN PATENT DOCUMENTS

CN    1871667 A    11/2006
CN    1993228 A    7/2007
(Continued)

OTHER PUBLICATIONS

KTA 1503.1—"Uberwachung der Abteilung gasfoermiger und an Schwebestoffen gebundener radioaktiver Stoffe—Teil 1 : Ueberwachung der Abteilung radioaktiver Stoffe mit der Kaminfortluft bei bestimmungsgemaessem Betrieb" Nov. 2012, [Safety Standards KTA 1503.1—Monitoring the Discharge of Radioactive Gases and Airborne Radioactive Particulates—Part 1: Monitoring the Discharge of Radioactive Matter with Stack Exhaust Air During Specified Normal Operation]—English version Nov. 2013.

*Primary Examiner* — Jack W Keith
*Assistant Examiner* — Daniel Wasil
(74) *Attorney, Agent, or Firm* — Laurence A. Greenberg; Werner H. Stemer; Ralph E. Locher

(57) ABSTRACT

An emission monitoring system for a venting system of a nuclear power plant is configured for low consumption of energy and high reliability. The emission monitoring system has a pressure relief line connected to a containment and contains a high-pressure section, a low-pressure section, and a sampling line. The sampling line opens into the low-pressure section of the pressure relief line and is guided from there to a functional path and through the sampling line steam flows. A jet pump containing a pump fluid connector, a suction connector and an outlet connector is provided. A pump fluid feed line has an inlet side opening into the high-pressure section of the pressure relief line and is guided
(Continued)

from there to the jet pump and connected to the pump fluid connector. A sample return line is guided from the functional path to the jet pump and connected to the suction connector.

12 Claims, 2 Drawing Sheets

(51) Int. Cl.
| | |
|---|---|
| *G21C 17/028* | (2006.01) |
| *G21D 3/04* | (2006.01) |
| *G01N 1/22* | (2006.01) |
| *G21C 13/02* | (2006.01) |
| *G21C 17/04* | (2006.01) |
| *G21C 17/10* | (2006.01) |
| *G21C 19/303* | (2006.01) |
| *G01N 1/10* | (2006.01) |
| *G01N 1/24* | (2006.01) |

(52) U.S. Cl.
CPC ......... *G21C 13/022* (2013.01); *G21C 17/028* (2013.01); *G21D 3/04* (2013.01); *G01N 2001/1037* (2013.01); *G01N 2001/242* (2013.01); *G21C 17/044* (2013.01); *G21C 17/10* (2013.01); *G21C 19/303* (2013.01); *Y02E 30/40* (2013.01)

(58) Field of Classification Search
USPC .................................... 376/256, 283, 314
See application file for complete search history.

(56) References Cited

U.S. PATENT DOCUMENTS

| | | | |
|---|---|---|---|
| 5,367,546 A | * | 11/1994 | Lau .......................... G01N 1/14 376/310 |
| 7,836,600 B2 | | 11/2010 | Chwalek et al. |
| 8,804,896 B2 | | 8/2014 | Eckardt et al. |
| 2008/0175345 A1 | | 7/2008 | Hill et al. |
| 2013/0008314 A1 | | 1/2013 | Guillemant et al. |

FOREIGN PATENT DOCUMENTS

| | | |
|---|---|---|
| CN | 101040348 A | 9/2007 |
| EP | 1298675 A1 | 4/2003 |
| JP | 2010145303 A | 7/2010 |
| JP | 2012230057 A | 11/2012 |
| WO | 2012025174 A1 | 3/2012 |

* cited by examiner

EMISSION MONITORING SYSTEM FOR A VENTING SYSTEM OF A NUCLEAR POWER PLANT

CROSS-REFERENCE TO RELATED APPLICATION

This is a continuation application, under 35 U.S.C. § 120, of copending international application No. PCT/EP2014/055804, filed Mar. 24, 2014, which designated the United States; this application also claims the priority, under 35 U.S.C. § 119, of German patent application No. DE 10 2013 207 595.2, filed Apr. 25, 2013; the prior applications are herewith incorporated by reference in their entirety.

BACKGROUND OF THE INVENTION

Field of the Invention

The invention relates to an emission monitoring system for a venting system of a nuclear power plant.

In case of a severe accident of a nuclear power plant, in addition to the release of steam, the release of large quantities of hydrogen can occur, in particular due to the known zirconium-water reaction. Without effective countermeasures, explosive (also detonation-capable) mixtures, which endanger the containment in the event of an uncontrolled reaction, are not to be precluded. Furthermore, in particular in the case of relatively small inerted boiling water reactor containments (typical volumes 5,000-15,000 $m^3$), due to the release of the non-condensible hydrogen together with steam, a rapid pressure increase occurs, which can go beyond the design pressure and can go up to the failure pressure of the containment.

To prevent overpressure failure of the containment, the plants have been equipped for some time with filtered pressure relief. In spite of the filtering, a release of radioactivity into the surroundings takes place to a certain extent during the pressure relief. This release is typically measured and recorded by an emission monitoring system. The ascertained data are used to inform the population and to derive accident measures.

The presently installed emission monitoring systems require a quantitatively substantial energy supply for operation for heating the sampling lines to avoid condensation and accumulation of aerosols. Furthermore, energy is required for the sample transport to the filters and the operation of the analyzers. The power supply (approximately 4-8 kW) can presently only be ensured via the emergency power diesel network. A desirable supply solely via batteries is difficult to implement due to the required battery capacity. Specifically, it would require a high expenditure for batteries and space. Furthermore, the plants are to be qualified for earthquake loads, which is complex because of the diesel generator sets and the associated fuel tanks and installation rooms. For accident sequences with complete failure of the internal power plant power supply (SBO=station blackout), the presently installed systems for monitoring are not available or are only available in limited form.

SUMMARY OF THE INVENTION

The present invention is based on the object of providing a remedy in this regard and specifying an emission monitoring system of the type mentioned at the outset, which, with a high level of reliability, availability, and quality of the measurement results, is configured for particularly low consumption of electrical energy.

Using the system according to the invention, emission monitoring can also be carried out during SBO events. The claimed emission monitoring system advantageously uses the thermo-hydraulic energy content of the venting exhaust gas stream for the sample conveyance and intrinsic medium heating to prevent condensation in the sampling lines. The optimized energy supply concept enables battery buffering from the failure of the normal operational power supply until the passive energy supply after the start of the containment venting process.

The essential advantages from the viewpoint of the user or operator are summarized hereafter:
a) autonomous processing of measurement and monitoring tasks with regard to gaseous emissions (exhaust gas monitoring) even in the case of SBO;
b) items of information on the activity release are also available during SBO;
c) information for deriving severe accident measures is provided;
d) low energy consumption for the operation of the online monitors (iodine, aerosols, noble gases);
e) energy supply by battery stores possible;
f) low battery capacity required;
g) small space requirement for the energy supply of the system;
h) the emission monitoring system collects a representative sample, which is proportional to the flow rate of the venting system;
i) regulation of the sample stream can be omitted; and actively turning on the sampling can be omitted, since the sampling is performed in a passively self-regulating manner by the venting stream.

Other features which are considered as characteristic for the invention are set forth in the appended claims.

Although the invention is illustrated and described herein as embodied in an emission monitoring system for a venting system of a nuclear power plant, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Identical or identically acting parts are provided with the same reference signs in both figures.

Figure 1:
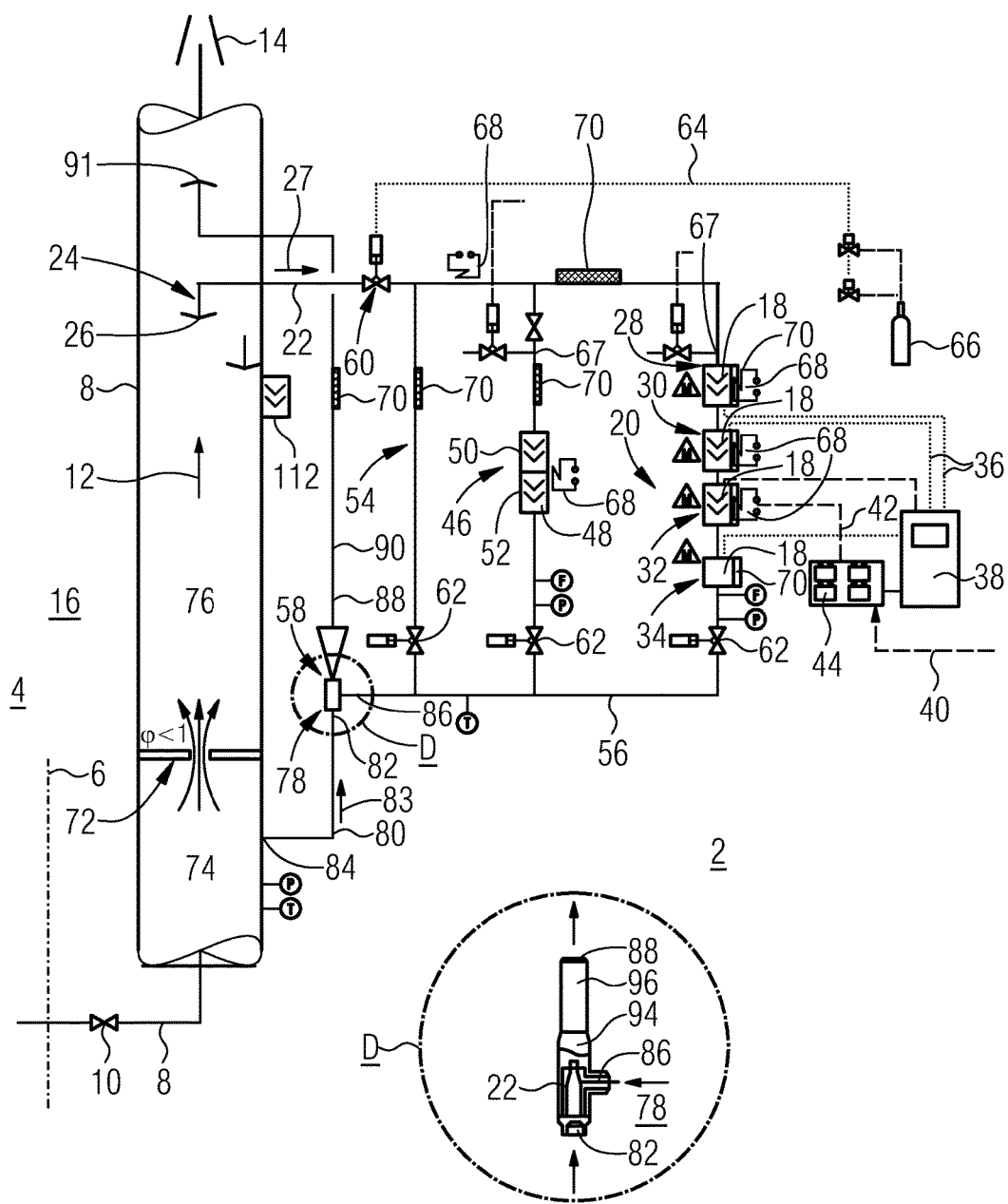
FIG. 1 is a schematic circuit diagram of an emission monitoring system for a venting system of a nuclear power plant in a first variant according to the invention.

Referring now to the figures of the drawings in detail and first, particularly to FIG. 1 thereof, there is shown an emission monitoring system 2, which is used for measuring and monitoring the predominantly gaseous emissions, which are released into the surroundings during the so-called venting of a nuclear power plant 4, in particular with regard to the radiological activity thereof.

Venting refers in this context to the controlled pressure reduction within the safety container 6, which is also referred to as a containment, and is only illustrated schematically and partially here, of the nuclear power plant 4 in the event of severe accidents having massive steam and gas release within the safety container 6, with correspondingly high overpressure in relation to the external surrounding atmosphere. For this purpose, a pressure relief line 8, which is also referred to as a vent line, is led out of the safety container 6, this line being closed in normal operation of the nuclear power plant 4 by a shutoff valve 10. To initiate the pressure relief, the shutoff valve 10 is opened, so that a predominantly gaseous pressure relief stream forms along the flow direction 12, which is released via a chimney 14 or the like into the surroundings. An overpressure in the containment is thus reduced to subcritical values.

To keep contamination of the surroundings as low as possible during the venting, various filter and/or washer units, in particular dry filters, wet washers, and/or sorbent filters, are in particular connected into the pressure relief line 8 upstream, optionally also downstream, of the section of the pressure relief line 8 which is picked out here in enlarged form, for the pressure relief stream, which is also referred to as a vent stream. This is referred to as filtered containment venting. Such units (not shown) are configured to substantially retain radioactive activities contained in the vent stream, in particular in the form of noble gases, iodine and iodine compounds, and aerosols. The entirety of all components provided for the venting operation is also referred to as a venting system 16.

Nonetheless, it cannot be entirely precluded that in specific severe accident scenarios, noteworthy quantities of activity will escape together with the vent stream into the surroundings, in particular in the case of old plants having inadequate retention units. In this case, at least temporary contamination of the power plant terrain threatens, which is to be taken into consideration during the planning and coordination of rescue measures. The emission monitoring system 2 is provided for this purpose, which collects a gas sample from the vent stream and supplies it to a number of analyzers 18. The analyzers 18, which preferably operate in through flow operation, perform, preferably in real time ("online monitoring") or in any case promptly, a measurement of the present content of noble gases, iodine and iodine compounds, and aerosols in the gas sample and/or ascertain the radiological activity to be attributed to these components. Furthermore, for example, gas analyzers can be integrated into an analysis section 20 for determining the hydrogen concentration.

Specifically, a sample taking line or in short a sampling line 22 is led for this purpose out of the pressure relief line 8, which guides the vent stream, and is attached or connected to the analysis section 20, which is arranged outside the pressure relief line 8. On an intake side, the sampling line 22 is provided with a sampling nozzle 24 or probe, which is situated inside the pressure relief line 8 and has an intake opening 26 protruding into the vent stream. Alternatively, a simple line branch from the pressure relief line 8 also comes into consideration. In this manner, a part of the vent stream is thus supplied as a sample stream in the flow direction 27 through the sampling line 22 to the analysis section 20.

The analysis section 20 is equipped in the exemplary embodiment here with a plurality of the above-mentioned, real-time capable analyzers 18, specifically an aerosol analyzer 28, an iodine or iodine compound analyzer 30, a noble gas analyzer 32, and a hydrogen analyzer 34, which all operate according to the through-flow principle and are connected in series with respect to flow. It is obvious that other and/or additional analyzers 18 can be provided, and that as an alternative to the series circuit, a parallel circuit of analyzers 18 or a combination of both line topologies can be implemented. Corresponding line branches and mergers can optionally be provided for this purpose.

Additionally/alternatively, such analyzers can be attached directly on/in the pressure relief line 8 for online monitoring, in particular with respect to iodine and aerosol components of the vent stream. For this purpose, for example, an expansion part having reduced wall thickness (approximately 3 mm) is located in the pressure relief line 8, preferably in the low-pressure portion 76 thereof (see below), to increase the sensitivity of the aerosol/iodine monitor 112, which is attached on the outer side, by way of the reduced shielding.

In the exemplary embodiment here, the analyzers 18 transmit the recorded measurement data via associated signal lines 36 to a shared control and pre-analysis unit 38, which can be installed, for example, in an emergency control room of the nuclear power plant 4. Alternatively, a plurality of decentralized analysis units can be installed. Under certain circumstances, the function of this unit can be restricted to data collection and optionally data processing, so that the actual analysis takes place in a downstream unit (not shown here). In addition, a remote transfer of raw and/or processed measurement data by telemetry or the like to an external observation station can be provided.

The power supply of the control and analysis unit 38 and—if necessary—the individual analyzers 18 is performed, with intact intrinsic power supply of the nuclear power plant 4, via a conventional plant power network 40 and, in the event of its failure, via an autonomous emergency power network 42, which is preferably activated according to the principle of an uninterruptible power supply (UPS) if needed. The emergency power network is preferably supplied by rechargeable batteries/accumulators 44, which can be recharged via the plant power network 40 if it is intact, but can also have a fuel cell unit and/or a diesel generator set.

In the exemplary embodiment according to FIG. 1, a filter section 46 having a number of filters/collectors 48 is connected to the sampling line 22 in a parallel circuit with respect to flow to the analysis section 20. For example, it is equipped with an aerosol filter 50 and an iodine filter/iodine compound filter 52. A partial stream of the sample stream collected via the sampling line 22 thus flows through the filter section 46. Online measurement is not provided for the filters/collectors 48 of the filter section 46; rather, they can be removed during the venting operation or at least after the abatement of the accident and studied with respect to the retained activity carriers. Even in the event of total failure of the online analyzers 18, a subsequently analyzable, summary documentation of the emissions released by the venting is still enabled.

Additionally or alternatively to the mentioned filters, for example, filters/collectors for H-3 (tritium) and C-14 (carbon) can be connected into the filter section 46.

Furthermore, a bypass section 54 is provided in a parallel circuit with respect to flow to the analysis section 20 and to the filter section 46. On the outlet side, all three partial lines discharge into a shared collection line or sample return line 56, in which a suction pump 58 or vacuum pump, which is to be described in greater detail hereafter, is connected further downstream. Alternatively to the nomenclature selected here, the entire line network of the sampling and analysis system between the sampling nozzle 24 and the suction pump 58 could be referred to in simplified form as the sampling line. This alternative nomenclature is used hereafter in conjunction with FIG. 2, inter alia, because fewer partial lines or line sections are to be differentiated with respect to terms therein.

To set or control or regulate the various partial streams, a plurality of shutoff and regulating valves are preferably provided in the line network of the sampling system. On the one hand, a settable shutoff valve 60 is provided upstream of the branches in the bypass section 54, the filter section 46, and the analysis section 20, using which the flow rate through the sampling line 22, that is to say the sample stream, can be set as a whole. On the other hand, the lines branching off from the sampling line 22, which form the mentioned functional sections 20, 46, 54, are themselves equipped with regulating valves 62 for setting the respective partial streams. These regulating valves 62 are arranged here in the exemplary embodiment downstream of the functional units, that is to say downstream of the filters/collectors 48 and the analyzers 18. Additionally or alternatively, such regulating and/or shutoff valves can be arranged upstream of the functional units, so that one or more partial lines can optionally be decoupled with respect to flow from the sampling line 22 in running operation, for example, for maintenance and replacement work and for inspection of the filters/collectors 48. In a particularly simple embodiment of the system, however, regulating and/or shutoff valves can also be substantially or even completely dispensed with, whereby the susceptibility to error and the control expenditure are reduced. In particular, active switching on of the sampling can be omitted if the shutoff valve 60 is dispensed with, since the sampling is then performed passively in a self-regulating manner by the venting stream and is therefore automatically activated.

Furthermore, the shutoff valve 60 in the sampling line 22, as indicated in FIG. 1, can be configured as a three-way valve having an additional line connection, namely for an inert gas line 64 or a flushing gas line. For example, an inert gas or flushing gas, in particular nitrogen $N_2$, can therefore be introduced as needed from a pressurized storage container 66, such as a pressurized gas bottle, into the sampling line 22 and admixed to the sample stream. With correspondingly selected valve setting of the three-way valve 60, the inert gas or flushing gas can also exclusively be conducted through the following section of the sampling line 22. In a similar manner, the individual partial lines of the functional sections can have line fittings 67 for inert gases, flushing gases, or also reagents for chemical conditioning of the respective partial stream, which are to be supplied as needed. Control or regulation of the significant valves is preferably performed via the central control unit 18, and alternatively manually.

For the most reliable possible measurement of the activities and gas compositions of interest, condensation of vaporized fractions in the sample stream and accumulation of aerosols on the path to the filters/collectors 48 of the filter section 46 and the analyzers 18 of the analysis section 20 are to be avoided as completely as possible.

For this purpose, in standby operation of the emission monitoring system 2, i.e., in normal operation of the nuclear power plant 4, preheating of the sampling line 22 and the partial lines leading to the filters 48 and analyzers 18 is provided at least on selected line sections and optionally on the filters 48 and analyzers 18 themselves. This standby heating is implemented in the emission monitoring system 2 according to FIG. 1 by an electric pipe trace heater, to which operating current is normally applied by the conventional plant power network 40 of the nuclear power plant 4. The associated heating coils/heating elements 68, which are laid around the pipe lines or are integrated in the pipe walls, are only indicated as examples at several points of the line network in FIG. 1. The heating power of the entire heating system is configured for a temperature to be ensured of the sample stream above the dewpoint temperature to be expected during measurement operation (approximately >150-200° C.).

In the case of a so-called station blackout situation with failure of the conventional plant power network 40, which typically exists in particular during the activation or during operation of the emission monitoring system 2, the above-mentioned emergency power network 42, based on a battery unit, a fuel cell unit, or a diesel generator set, at least initially takes over the power supply of the electrical pipe heating and therefore the compensation of the unavoidable heat losses during the sample transport.

To keep the heat losses as low as possible (approximately <500 W), the sampling line 22, the partial lines branching off therefrom to the functional units (filters/collectors 48 and analyzers 18), and the functional units themselves are provided as completely as possible, but at least in some relevant portions and regions, with thermal insulation, in particular in the form of an insulation jacket 70, which is only schematically indicated at several points in FIG. 1. In addition, materials having poor heat conductivity are preferably used in the region of the pipe walls or housing walls.

To avoid aerosol accumulation on the walls of the flow path, the sampling line 22 and the partial lines branching off therefrom to the functional units are preferably embodied having internal Teflon coating or aluminum coating or in hydraulically smooth, electropolished stainless steel.

To keep the capacity requirements for the emergency power supply 42 or the energy stores thereof as low as possible and nonetheless to ensure reliable sample transport to the functional modules while preventing vapor condensation, an array of measures is provided, which bring about the design of the emission monitoring system 2 according to FIG. 1 to form a substantially passive or semi-passive system (of course, the analysis and control unit 38 and the analyzers 18 generally require a certain quantity of electrical current, so that complete passivity in the sense of complete decoupling from the emergency power network 42 is only implementable with difficulty in this variant). These measures will now be described in detail.

On the one hand, a throttle portion, in the form of a throttle orifice 72 here, is arranged in the pressure relief line 8 which guides the vent stream. Upstream of the throttle orifice 72, the gas pressure approximately corresponds to the containment internal pressure of the atomic plant 4, typically of 3 to 6 bar absolute at the beginning of the venting, possibly reduced by a pressure drop of up to 1 or 2 bar, in the line sections connected upstream with respect to flow, including filter and/or washer units. A pressure reduction to approximately the ambient pressure of approximately 1 bar absolute is performed by the throttle orifice 72. Therefore, a high-pressure portion 74 of the pressure relief line 8 upstream of the throttle orifice 72 and a low-pressure portion 76 downstream of the throttle orifice 72 can be referred to.

Passive drying and overheating of the vent stream take place due to the throttling, so that, in sampling operation with open shutoff valve 60 in the sampling line 22, through the sampling nozzle 24, which is preferably arranged downstream of the throttle orifice 72, an overheated sample is introduced into the sampling line 22, the vapor fraction of which already has a sufficient dewpoint distance (with relative humidity <1).

In addition, by way of a suction pump 58, which is connected in the collection line 56 leading away from the filters 48 and the analyzers 18, a partial vacuum, which drives or assists the sample transport, is generated in the upstream portions of the line system provided for the sampling and analysis. By way of the partial vacuum, the vapor fraction in the sample stream is led further by isenthalpic relaxation into the overheating region of the phase diagram, which describes the thermodynamics. The dewpoint temperature is reduced in this way below the prevailing saturation vapor temperature before the throttle orifice 72. The electrical heating can be completely deactivated and removed from the energy balance due to the sampling line 22, including filter section 46 and analysis section 20, which is heated using the isenthalpic relaxed intrinsic medium. Sampling and heating now take place—in any case after a brief initial startup phase, in which the electrical heating can also be switched on as a supplement under certain circumstances—completely passively over the entire venting procedure.

The suction pump 58 can in principle be an electrically driven pump, which is supplied with operating power via the plant power network 40 or the emergency power network 42 of the nuclear power plant 4. However, it is particularly advantageous in the meaning of the desired passive system design if it is driven by the existing flow energy of the vent stream in the pressure relief line 8, as exists in particular in the high-pressure portion thereof.

For this purpose, the suction pump 58 of the emission monitoring system 2 according to FIG. 1 is embodied as a jet pump 78, sometimes also referred to as an ejector. A partial stream of the vent stream from the high-pressure portion 74—i.e., the portion upstream of the throttle orifice 72—of the pressure relief line 8 of the nuclear power plant 4 is collected as the propellant. That is to say, a pressure resistant propellant supply line 80 is led from the high-pressure portion 74 of the pressure relief line 8 to the propellant fitting 82 of the jet pump 78, through which flow occurs in the flow direction 83. The intake opening 84 of the propellant supply line 80 can be formed, as indicated in FIG. 1, as a simple branch from the pressure relief line 8 or, as in the preferred embodiment of the sampling line 22, as a sampling nozzle protruding into the flow channel.

The collection line or sample return line 56 for the sample stream on the outlet side of the filter section 46, the analysis section 20, and optionally the bypass section 54 of the sampling line system is connected to the suction fitting 86 or suction connecting piece of the jet pump 78. An outlet line or return line 90 is connected to the outlet fitting 88 of the jet pump 78, which is led back at the other end, the outlet end 91, into the pressure relief line 8 in a preferred embodiment, specifically into the low-pressure portion 76 thereof, downstream of the throttle orifice 72, in particular downstream of the sampling nozzle 24 of the sampling line 22.

The jet pump 78 can be embodied in conventional construction and, at the propellant intake, can have a propellant nozzle 92, further downstream a mixing chamber 94, in which the propellant jet meets the suction means sucked in from the circumferential region, and at the outlet side an optional diffuser 96 for partial pressure reclamation, as indicated in detail D of FIG. 1. Alternatively, a design like a simple Venturi nozzle 97 is also possible, at the constriction point or throat 98 of which the suction fitting 86 is formed as an opening in the pipe wall. Such a configuration is illustrated in detail E of FIG. 2 (the optional envelope by a jacket pipe of the sampling line 22 additionally depicted therein will be described in greater detail hereafter).

According to the known functional principle of the jet pump 78, a partial vacuum for suctioning in the sample stream is generated in the nozzle section or throat 98 thereof by the conversion of pressure energy into flow velocity. The sucked-in sample stream is primarily entrained by momentum transfer from the propellant stream and mixes with it at the same time. The resulting mixture of propellant and suction means, which is at relatively low pressure—in both cases partial streams of the vent stream here—then leaves the jet pump 78 via the outlet fitting 88 thereof and the return line 90 connected thereto and is advantageously unified again, as already described above, with the remaining vent stream and released together with it into the surroundings. The sampling and the sample transport are therefore performed completely passively by the existing flow energy of the vent stream, wherein passive overheating of the sample stream is additionally ensured.

The variant of the emission monitoring system 2 illustrated in FIG. 2 differs as follows from the variant illustrated in FIG. 1.

On the one hand, no aerosol/iodine monitoring performed online is provided here. The analysis section 20 is thus omitted. The bypass section 54 is also not provided. Only the filter section 46 having aerosol filters 50 and/or iodine filters 52 is implemented. Instead of an emission monitoring system 2, an emission documentation system can also be referred to in this variant. Such alterations could also be implemented in the variant according to FIG. 1, of course.

In addition, the entire sampling line 22 is now led from the sampling nozzle 24 via the aerosol filters 50 and/or iodine filters 52 up to the suction fitting 86 of the jet pump 78 in an enveloping jacket pipe 100, so that a heating medium can flow through the intermediate space between the outer wall of the sampling pipe 102 and the inner wall of the jacket pipe 100. The sampling pipe 102 is advantageously embodied in this embodiment using a material (for example, aluminum) having high thermal conductivity, while the jacket pipe 100 preferably has poor thermal conductivity and/or is provided with a thermal insulation jacket 104, to promote the heat transfer from the heating medium to the sample stream, on the one hand, and to minimize the heat dissipation to the external surroundings, on the other hand.

A partial stream of the vent stream from the vent line 8 is advantageously branched off as the heating medium. For this purpose, the jacket pipe 100 has, for example, as shown in detail F, a ring-shaped intake opening 106 for the comparatively hot vent gas in the region of the sampling nozzle 24 of the sampling line 22. In this embodiment, therefore, the sampling nozzle 24 can already be heated. The vent gas, which acts as the heating medium, subsequently flows through the intermediate space between sampling pipe 102 and jacket pipe 100 in the same direction as the sample stream and thus causes the desired superheating of the sample in the sampling line 22 including the filter section contained therein having the filters/collectors 48. Downstream of the filter section, the heating stream and the sample stream are advantageously brought together, for example, as shown in detail E through a slotted transfer 108 in the pipe wall of the sampling pipe 102, and after/with mutual mixing are sucked in jointly at the suction fitting 86 of the jet pump 78. To avoid undesired backflow into the sampling pipe 102, a throttle orifice 109 can be arranged in the sampling pipe 102 upstream of the transfer 108.

In the described manner, in particular with still closed sampling line 22 in standby operation of the emission monitoring system 2, preheating of the sampling line 22 can be performed by solely passive suctioning in of the hot vent gas stream via the jacket pipe 100. This heating is also maintained later in the actual sampling operation with open sampling line 22. Electrical preheating of the sampling line 22, which is indicated in FIG. 2 by optional heating elements 110, can be completely omitted with suitable design and dimensioning of the flow and temperature conditions.

Such a design of the pipe heating having jacket pipes 100, through which vent gas flows, is also possible in principle in the more complex system variant according to FIG. 1, at least for individual partial lines. However, complete coverage of the heating demand in this manner is more difficult to achieve in particular in regard to the analysis section 20. Because of the variety of pipe branches and mergers, the design effort would also be substantial therein, so that this design suggests itself more for systems which are kept simple, as in FIG. 2.

Figure 2:
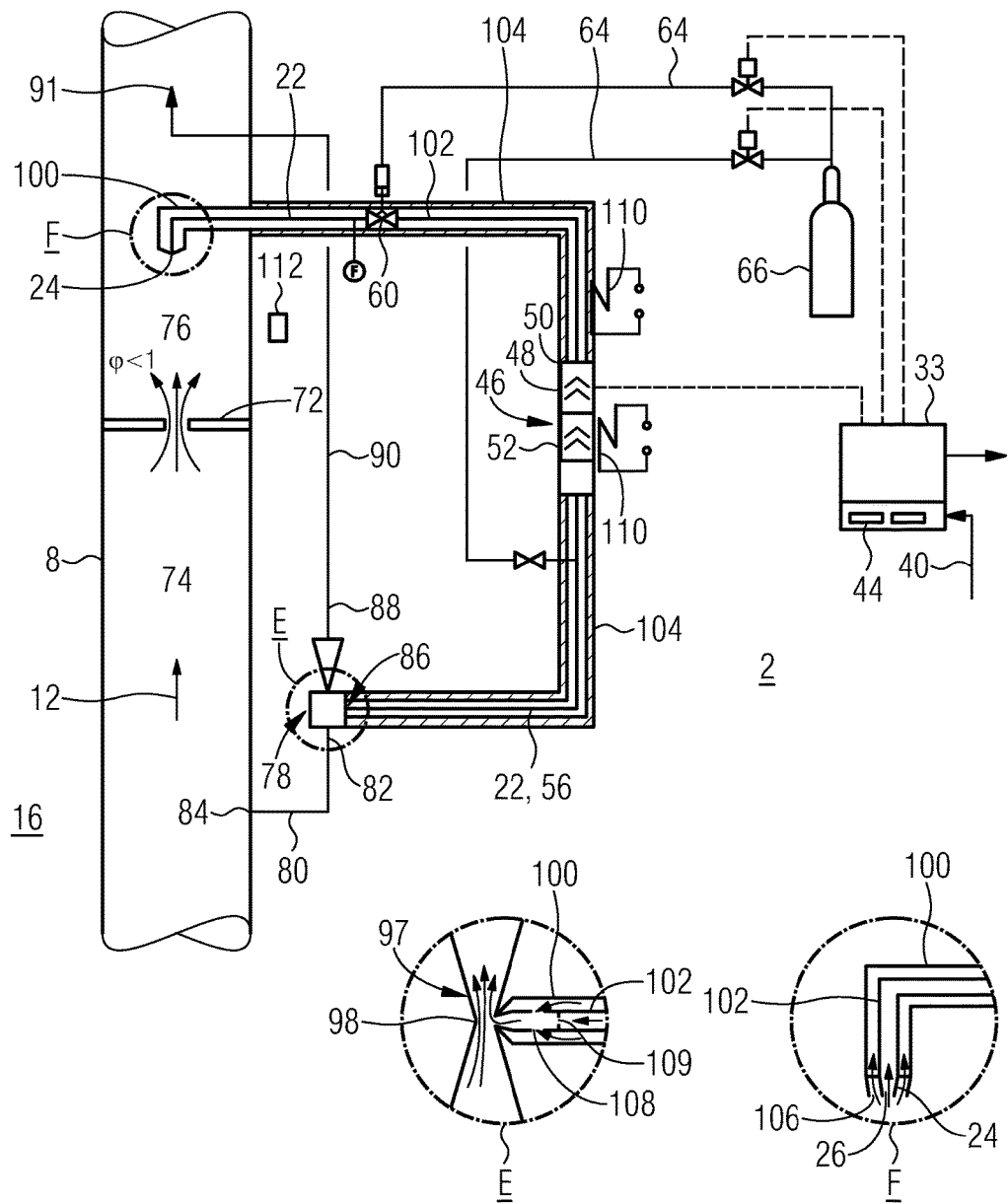
FIG. 2 is a schematic circuit diagram of an emission monitoring system for a venting system of a nuclear power plant in a second variant.

As already mentioned, various combinations of the individual components and partial sections provided in FIG. 1 and FIG. 2 can be implemented. A focal point in online measured value acquisition is placed in particular on the emitted radioactive noble gases. The noble gas analyzer 32, which is advantageously arranged in the analysis section 20, has a robust gamma sensor for this purpose, for example. The measured values which are preferably continuously recorded and transmitted online by the noble gas analyzer 32 enable conclusions about the mass flows and concentration of the noble gases contained in the vent stream and of the corresponding nuclide-specific activity rates. The quantity of the radioactive aerosols and iodine components contained in the vent stream and the contribution thereof to the activity release can be ascertained therefrom in the sense of a modeled rough estimate or simulation quickly (ideally in quasi-real time), without having to carry out online monitoring for these components themselves. Sophisticated simulation programs and the like are available for this purpose, which take into consideration the respective reactor type. That is to say, the aerosol analyzers 28 operating online and the iodine analyzers 30 from FIG. 1 can optionally be omitted, without having to accept substantial losses with respect to the analysis quality.

Nonetheless, a representative sampling with respect to the aerosol and iodine components and also optionally H-3 and C-14 in the filters/collectors 48 of the filter section 46, which are configured for correspondingly high temperatures and pressures of the sample stream and are therefore outstandingly robust, can be performed during the venting. After ending the venting process, an analysis of the collected activities can then be performed in a laboratory (in particular for documentation or preservation of evidence of the activity emissions). On the basis of this subsequent analysis, a correction of the measured values which were previously captured online and/or the nuclide-specific outflow and activity rates calculated on the basis of models can optionally be performed. The circumstance is thus also taken into consideration that the long-lived radioactive isotopes, for example, I-131 or Cs-137, which are particularly important for evaluating the environmental stress, can possibly only be directly captured metrologically during the venting with difficulty, because the short-lived noble gas decomposition products such as Rb-88 or Cs-137 dominate the vent stream with respect to radiation at this point in time.

The following is a summary list of reference numerals and the corresponding structure used in the above description of the invention:

2 emission monitoring system
4 nuclear power plant
6 safety container/containment
8 pressure relief line/vent line
10 shutoff valve
12 flow direction
14 chimney
16 venting system
18 analyzer
20 analysis section
22 sampling line
24 sampling nozzle
26 intake opening/intake mouth
27 flow direction
28 aerosol analyzer
30 iodine analyzer
32 noble gas analyzer
34 hydrogen analyzer
36 signal line
38 control and/or analysis unit
40 plant power network
42 emergency power network
44 battery/accumulator
46 filter section
48 filter/collector
50 aerosol filter
52 iodine filter
54 bypass section
56 collection line/sample return line
58 suction pump
60 shutoff valve/three-way valve
62 regulating valve
64 inert gas line/flushing gas line
66 storage container
67 line fitting
68 heating coil/heating element
70 insulation jacket
72 throttle orifice
74 high-pressure portion
76 low-pressure portion
78 jet pump
80 propellant supply line
82 propellant fitting
83 flow direction
84 intake opening
86 suction fitting
88 outlet fitting
90 return line
91 outlet end/outlet mouth
92 propellant nozzle
94 mixing chamber
96 diffuser
97 Venturi nozzle
98 throat
100 jacket pipe
102 sampling pipe
104 thermal insulation jacket
106 intake opening
108 transfer
109 throttle orifice
110 heating element
112 aerosol/iodine monitor M online monitoring
N$_2$ nitrogen
D, E, F details

The invention claimed is:

1. An emission monitoring system for a venting system of a nuclear power plant, the nuclear power plant having a containment, the emission monitoring system comprising:
   a pressure relief line configured to receive emissions from the containment of the nuclear power plant and having a high-pressure portion and a low-pressure portion;
   a functional section having at least one element selected from the group consisting of an online analyzer and a filter;
   a sampling line having an intake mouth opening into said low-pressure portion of said pressure relief line and is lead therefrom to said functional section, through which sample stream can flow;
   a jet pump having a propellant fitting, a suction fitting, and an outlet fitting;
   a propellant supply line having an intake side opening into said high-pressure portion of said pressure relief line and is led from there to said jet pump and is connected to said propellant fitting; and
   a sample return line leading from said functional section to said jet pump and is connected to said suction fitting.

2. The emission monitoring system according to claim 1, further comprising a return line leading from said outlet fitting of said jet pump into said low-pressure portion of said pressure relief line and discharges therein on an outlet side.

3. The emission monitoring system according to claim 2, wherein said sample return line has an outlet mouth disposed, viewed in a flow direction of vent stream in said pressure relief line, after said intake mouth of said sampling line.

4. The emission monitoring system according to claim 1, further comprising a jacket pipe, at least one of said sampling line or said sample return line are led in said jacket pipe, through which a heating medium can flow.

5. The emission monitoring system according to claim 4, wherein said jacket pipe is provided such that a partial stream of vent stream which is branched off is active as the heating medium in said pressure relief line.

6. The emission monitoring system according to claim 5, wherein the heating medium is oriented in a same direction as the sample stream.

7. The emission monitoring system according to claim 1, wherein said functional section is disposed outside of said pressure relief line.

8. The emission monitoring system according to claim 1, wherein said functional section has a filter section with said filter, said filter including an aerosol filter and/or an iodine filter.

9. The emission monitoring system according to claim 1, wherein said functional section contains an analysis section having said online analyzer being one of a plurality of online analyzers selected from the group consisting of an aerosol analyzer, a noble gas analyzer, and an iodine analyzer, said online analyzers are configured for capturing associated radiological activities.

10. The emission monitoring system according to claim 1, further comprising a throttle portion disposed between said high-pressure portion and said low-pressure portion.

11. The emission monitoring system according to claim 10, wherein said throttle portion is a throttle orifice.

12. A nuclear power plant, comprising:
   a venting system; and
   an emission monitoring system according to claim 1 and connected to said venting system.

\* \* \* \* \*